US011154662B2

(12) United States Patent
Nguyen

(10) Patent No.: US 11,154,662 B2
(45) Date of Patent: *Oct. 26, 2021

(54) CAP WITH HEMISPHERE PORTION FOR MEDICAL INJECTOR

(71) Applicant: Becton Dickinson France S.A.S., Le Pont-de-Claix (FR)

(72) Inventor: Emilie Nguyen, Garges lès Gonesse (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 154 days.

This patent is subject to a terminal disclaimer.

(21) Appl. No.: 16/378,920

(22) Filed: Apr. 9, 2019

(65) Prior Publication Data
US 2019/0231988 A1 Aug. 1, 2019

Related U.S. Application Data

(63) Continuation of application No. 15/372,630, filed on Dec. 8, 2016, now Pat. No. 10,300,216.

(60) Provisional application No. 62/264,518, filed on Dec. 8, 2015.

(51) Int. Cl.
A61M 5/32 (2006.01)
A61M 5/315 (2006.01)

(52) U.S. Cl.
CPC ........ *A61M 5/3213* (2013.01); *A61M 5/3202* (2013.01); *A61M 5/3204* (2013.01); *A61M 5/31511* (2013.01)

(58) Field of Classification Search
CPC .............. A61M 5/3213; A61M 5/3202; A61M 5/3204; A61M 5/31511; A61M 2205/0216
See application file for complete search history.

(56) References Cited

U.S. PATENT DOCUMENTS

| 2,131,687 A | 9/1938 | Kaplan |
| D239,021 S | 3/1976 | D'Alo |
| 4,365,626 A | 12/1982 | House |
| 4,636,201 A | 1/1987 | Ambrose et al. |
| 4,832,695 A | 5/1989 | Rosenberg et al. |

(Continued)

FOREIGN PATENT DOCUMENTS

| CN | 1816368 A | 8/2006 |
| EP | 2923716 A1 | 9/2015 |

(Continued)

*Primary Examiner* — Theodore J Stigell
(74) *Attorney, Agent, or Firm* — The Webb Law Firm

(57) ABSTRACT

A medical injector includes an injector housing defining a reservoir, a plunger rod, and a stopper engaged with a portion of the plunger rod, the stopper being slidably disposed within the reservoir and sized relative to an interior of the injector housing to provide sealing engagement with a sidewall of the injector housing. The medical injector further includes a needle having a sharpened first end and a second end in communication with the reservoir, a first cap covering the sharpened first end of the needle, and a second cap covering at least a part of the first cap. The second cap includes a body having a proximal end, a distal end, and a hemispherical member including a gripping component. The second cap is engaged with the first cap such that removal of the second cap simultaneously removes the first cap from the first end of the needle.

15 Claims, 7 Drawing Sheets

(56) References Cited

U.S. PATENT DOCUMENTS

| | | | |
|---|---|---|---|
| 4,872,721 A | 10/1989 | Sniadach | |
| 4,898,588 A * | 2/1990 | Roberts | A61M 3/0287 604/187 |
| 4,929,232 A | 5/1990 | Sweeney et al. | |
| 4,982,842 A * | 1/1991 | Hollister | A61M 5/3216 206/365 |
| 4,986,817 A * | 1/1991 | Code | A61M 5/3213 604/192 |
| 5,183,469 A | 2/1993 | Capaccio | |
| D337,157 S | 7/1993 | Ortiz | |
| D375,788 S | 11/1996 | Potts et al. | |
| D380,262 S | 6/1997 | Van Funderburk et al. | |
| 5,647,849 A | 7/1997 | Kalin | |
| D427,308 S | 6/2000 | Zinger | |
| D473,646 S | 4/2003 | Baillargeon et al. | |
| 6,582,397 B2 | 6/2003 | Alesi et al. | |
| D483,487 S | 12/2003 | Harding et al. | |
| D486,225 S | 2/2004 | Gay, III | |
| D492,774 S | 7/2004 | Cindrich et al. | |
| D497,990 S | 11/2004 | Jutila | |
| D505,200 S | 5/2005 | Simpson et al. | |
| 7,059,327 B2 | 6/2006 | Worthington | |
| D605,755 S | 12/2009 | Baxter et al. | |
| D607,558 S | 1/2010 | Abry et al. | |
| D629,510 S | 12/2010 | Grunhut | |
| D633,199 S | 2/2011 | MacKay et al. | |
| D637,713 S | 5/2011 | Nord et al. | |
| D642,261 S | 7/2011 | York et al. | |
| D655,000 S | 2/2012 | Mirigian | |
| D655,017 S | 2/2012 | Mosler et al. | |
| D679,008 S | 3/2013 | Schroeder et al. | |
| D681,230 S | 4/2013 | Mosler et al. | |
| D702,343 S | 4/2014 | Dale et al. | |
| D702,835 S | 4/2014 | Vinchon | |
| D709,753 S | 7/2014 | Guala | |
| 8,858,507 B2 | 10/2014 | Nielsen et al. | |
| D718,439 S | 11/2014 | Woehr et al. | |
| D738,494 S | 9/2015 | Kashmirian | |
| D750,239 S | 2/2016 | Pappalardo | |
| D750,258 S | 2/2016 | Crossley | |
| D750,779 S | 3/2016 | Ahluwalia et al. | |
| D751,192 S | 3/2016 | She et al. | |
| D755,966 S | 5/2016 | Ahluwalia et al. | |
| D755,967 S | 5/2016 | Ahluwalia et al. | |
| D757,258 S | 5/2016 | Weißhaupt et al. | |
| D757,935 S | 5/2016 | Solingen et al. | |
| D760,891 S | 7/2016 | Nakamura et al. | |
| D761,422 S | 7/2016 | Row et al. | |
| D765,241 S | 8/2016 | Holland | |
| D768,850 S | 10/2016 | Rozwadowski et al. | |
| D768,851 S | 10/2016 | Rozwadowski et al. | |
| 10,300,216 B2 * | 5/2019 | Nguyen | A61M 5/3213 |
| 10,335,556 B2 * | 7/2019 | Vedrine | A61M 5/3293 |
| 2001/0044606 A1 | 11/2001 | Inkpen et al. | |
| 2004/0133172 A1 | 7/2004 | Wilkinson | |
| 2004/0210197 A1 | 10/2004 | Conway | |
| 2007/0129686 A1 | 6/2007 | Daily et al. | |
| 2008/0154192 A1 * | 6/2008 | Schraga | A61M 5/50 604/110 |
| 2008/0228147 A1 | 9/2008 | David-Hegerich et al. | |
| 2009/0312705 A1 | 12/2009 | Grunhut et al. | |
| 2011/0092915 A1 | 4/2011 | Olson et al. | |
| 2012/0029439 A1 * | 2/2012 | Hudson | A61M 5/3202 604/192 |
| 2012/0302965 A1 * | 11/2012 | Cronenberg | A61M 5/3276 604/198 |
| 2013/0085453 A1 | 4/2013 | Manke et al. | |
| 2014/0261877 A1 * | 9/2014 | Ivosevic | A61J 1/201 141/27 |
| 2015/0045729 A1 | 2/2015 | Denzer et al. | |
| 2015/0165129 A1 | 6/2015 | Row et al. | |
| 2016/0144132 A1 | 5/2016 | Scanlon | |
| 2016/0193428 A1 | 7/2016 | Perthu | |
| 2017/0014578 A1 | 1/2017 | Bunch | |
| 2018/0318519 A1 * | 11/2018 | Lee | A61M 5/32 |

FOREIGN PATENT DOCUMENTS

| | | |
|---|---|---|
| WO | 03051423 A2 | 6/2003 |
| WO | 2005025636 A2 | 3/2005 |
| WO | 2014150201 A1 | 9/2014 |
| WO | 2014154498 A1 | 10/2014 |
| WO | 2015014363 A2 | 2/2015 |
| WO | 2015028488 A1 | 3/2015 |
| WO | 2015073740 A2 | 5/2015 |
| WO | 2015105511 A1 | 7/2015 |
| WO | 2015123096 A1 | 8/2015 |

* cited by examiner

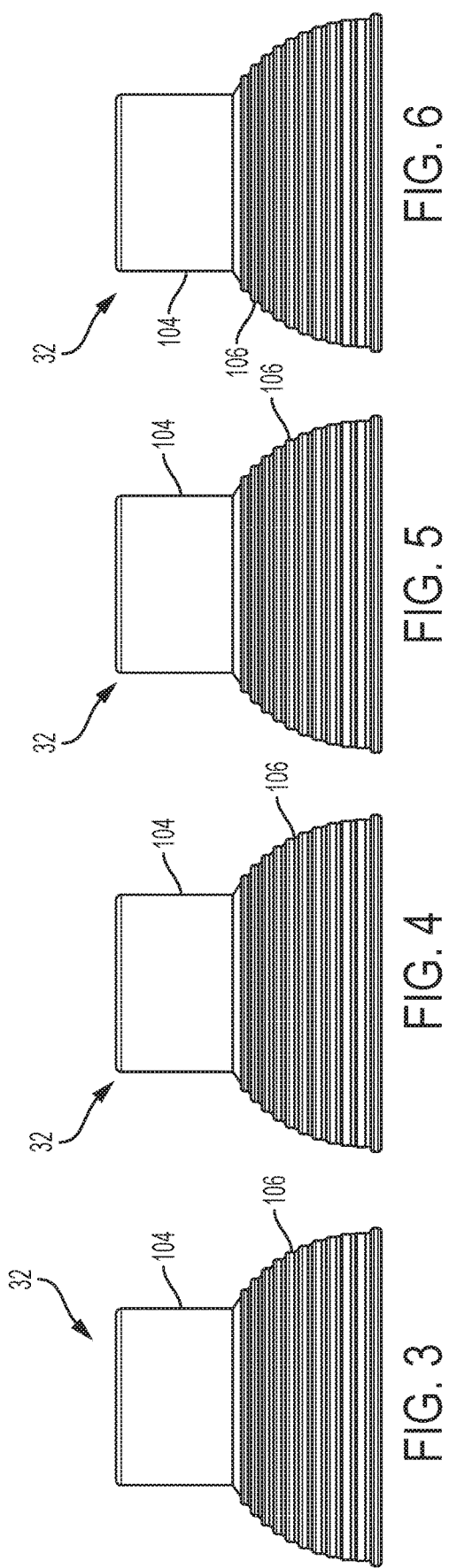
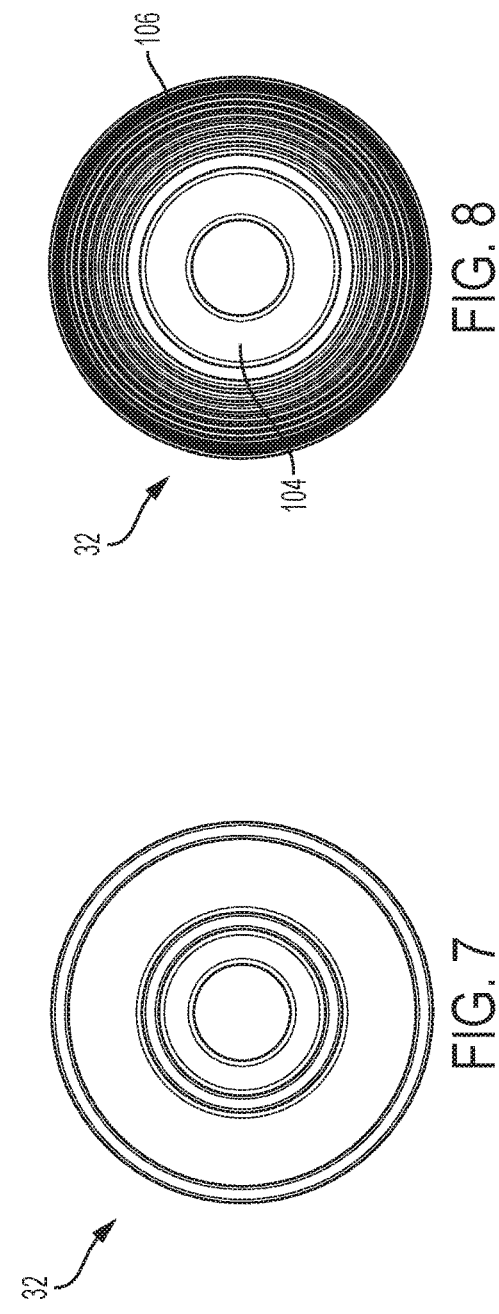

CAP WITH HEMISPHERE PORTION FOR MEDICAL INJECTOR

CROSS REFERENCE TO RELATED APPLICATIONS

This application is a continuation of U.S. patent application Ser. No. 15/372,630 filed Dec. 8, 2016, which claims the benefit of U.S. Provisional Application No. 62/264,518 filed Dec. 8, 2015, the disclosures of each of which are incorporated herein by reference in their entirety.

BACKGROUND OF THE INVENTION

Field of the Disclosure

The present disclosure relates generally to medical injector devices for delivery of a fluid or liquid medicament. More particularly, the present disclosure relates to a safety cap and/or a cap remover for a medical injector device or a syringe.

Description of the Related Art

Medical injectors and syringes are well known in the prior art. Medical injectors may include auto-injectors and pen injectors which are capable of delivering selected doses of fluids including liquid medicaments or vaccinations to a patient. Medical injectors typically are configured to receive a standard pre-filled glass or plastic syringe tipped with an injection needle. These devices may include a drive member for advancing a plunger into a syringe barrel to expel a liquid medicament out through the needle. The required manipulation of a standard prior art hypodermic syringe can be inconvenient, particularly where the injection is self-administered in a public environment, and many medication delivery pens, pen injectors, or other self-injectors have been developed to facilitate self-administration of injections.

In order to maintain sterility prior to use and to reduce the risk of incurring an accidental needle-stick, protection of the needle tip is important. Medical injectors are typically supplied with a rubber or plastic cap which guards the needle prior to use. Immediately prior to use, the user must remove the protective cap from the injector, such as by using the cap protector of the present invention.

SUMMARY OF THE INVENTION

In accordance with an embodiment of the present invention, a medical injector includes an injector housing defining a reservoir, a plunger rod, and a stopper engaged with a portion of the plunger rod, the stopper being slidably disposed within the reservoir and sized relative to an interior of the injector housing to provide sealing engagement with a sidewall of the injector housing. The medical injector further includes a needle having a sharpened first end and a second end in communication with the reservoir, a first cap covering the sharpened first end of the needle, and a second cap covering at least a part of the first cap. The second cap includes a body having a proximal end, a distal end, and a hemispherical member including a gripping component. The second cap is engaged with the first cap such that removal of the second cap simultaneously removes the first cap from the first end of the needle. The medical injector may further include a liquid medicament disposed within the reservoir.

The second cap may engage the first cap via a friction fit. For example, the second cap may include an interior wall defining a cavity in a proximal end of the second cap, such that the cavity is sized and shaped to receive at least a portion of the first cap. A protrusion extends inwardly from the interior wall of the second cap and is adapted to frictionally engage the first cap. The protrusion may be an annular ring.

The first cap may be formed from a first material and the second cap may be formed from a second material, the first material being different from the second material. In one embodiment, the first cap is formed from an elastomeric sleeve disposed over at least the sharpened first end of the needle. The second material may be harder than the first material.

The hemispherical member may be provided adjacent the distal end of the second cap body. The gripping component may include at least one rib extending at least partially about the hemispherical member and at least one trough extending at least partially about the hemispherical member adjacent the at least one rib. In one embodiment, the gripping component includes a plurality of ribs and a plurality of troughs extending circumferentially about the hemispherical member such that the plurality of ribs and the plurality of troughs alternate from a proximal end to a distal end of the hemispherical member. The hemispherical member may further include a flange having a substantially flat distally directed surface.

In accordance with another embodiment of the present invention, a cap remover includes a body having a proximal end, a distal end, and an interior wall defining a cavity within the proximal end of the cap body, the cap remover body having a hemispherical member including a gripping component. The gripping component includes a rib extending circumferentially about the hemispherical member and a trough extending circumferentially about the hemispherical member. The cavity is sized and shaped to accommodate a cap disposed on a medical injector at least partially therein. With the cap received within the cavity, the cap remover may remove the cap from the medical injector. The cap remover may further include a protrusion extending inwardly from the interior wall of the cap remover body. The protrusion is adapted to frictionally engage the cap. With the protrusion of the cap remover body engaged with the cap, the cap remover body may disengage the cap from the medical injector upon application of a distally directed force to the cap remover body.

In one embodiment, the gripping component includes a plurality of ribs and a plurality of troughs alternating from a proximal end of the hemispherical member to a distal end of the hemispherical member. The hemispherical member may further include a flange having a substantially flat distally directed surface.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 3 is a first elevation view of a cap remover in accordance with an embodiment of the present invention.

FIG. 4 is a second elevation view of a cap remover in accordance with an embodiment of the present invention.

FIG. 5 is a third elevation view of a cap remover in accordance with an embodiment of the present invention.

FIG. 6 is a fourth elevation view of a cap remover in accordance with an embodiment of the present invention.

FIG. 7 is a fifth elevation view of a cap remover in accordance with an embodiment of the present invention.

FIG. 8 is a sixth elevation view of a cap remover in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
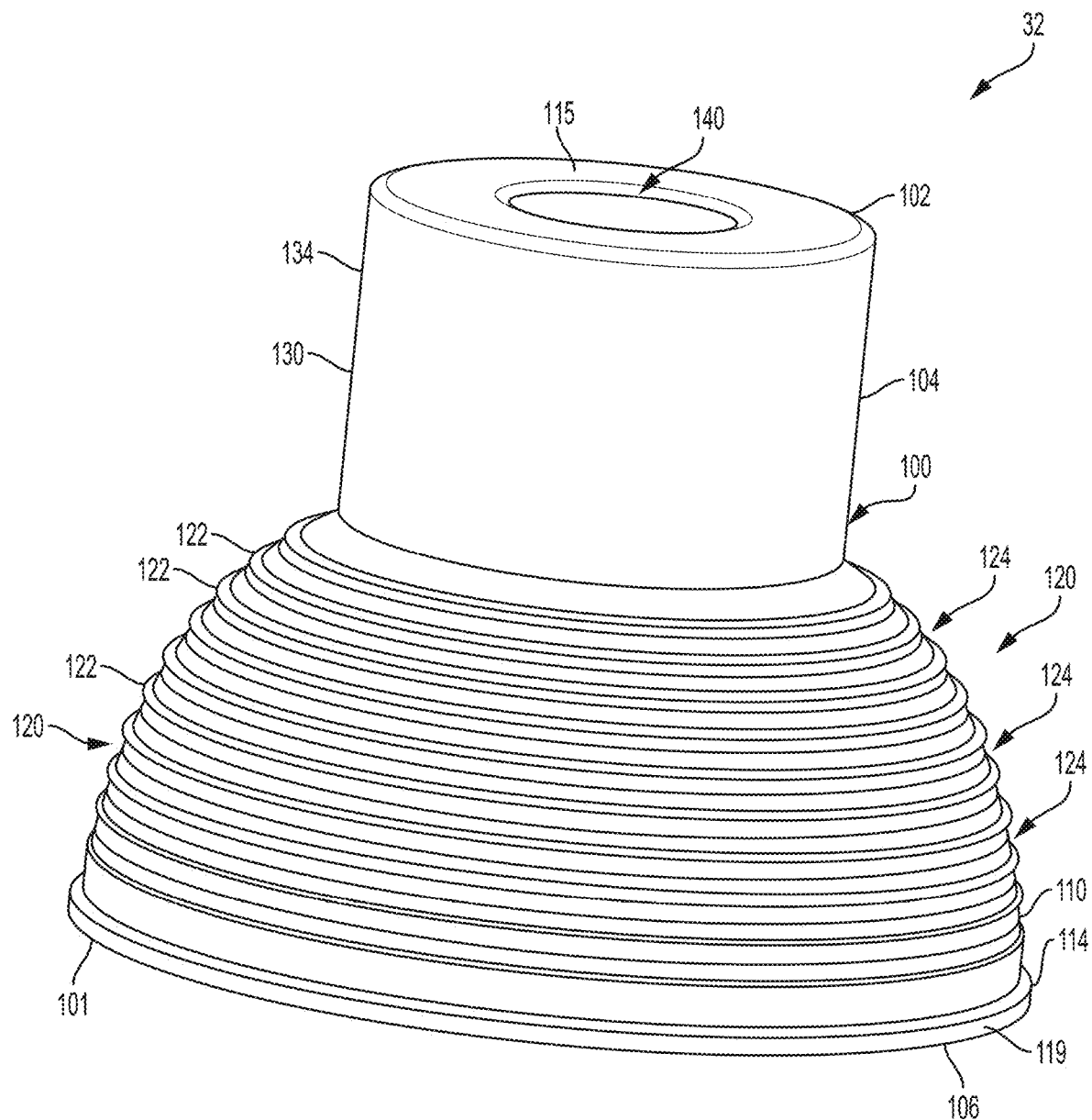
FIG. 1 is a perspective view of a cap remover in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a medical injector adapted for contact with a patient and/or engagement with a separate device, and "proximal" refers to the opposite direction of distal, i.e., away from the end of a medical injector adapted for engagement with the separate device. For purposes of this disclosure, the above-mentioned references are used in the description of the components of a medical injector in accordance with the present disclosure.

Figure 9:
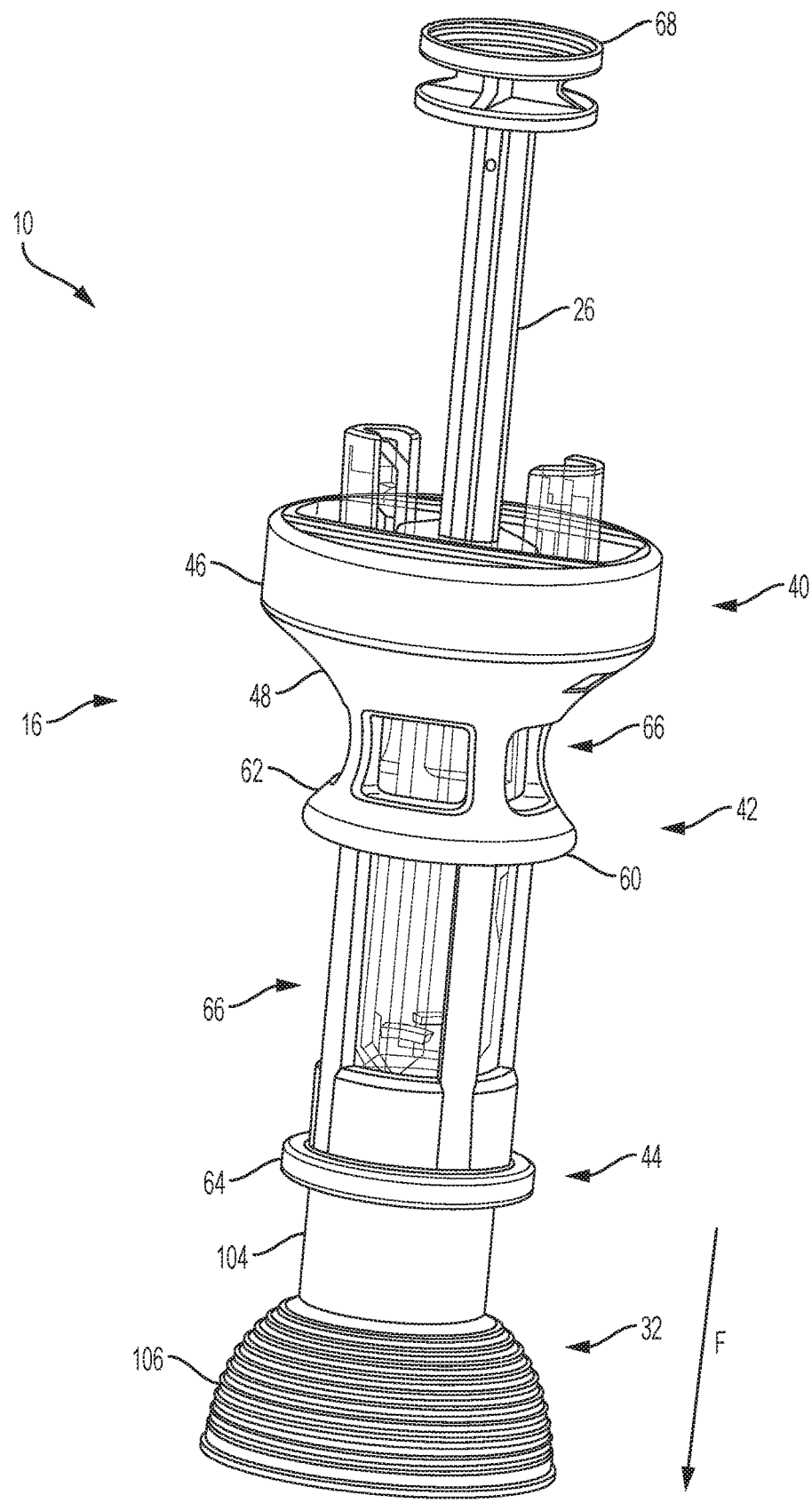
FIG. 9 is a perspective view of a medical injector with a cap remover in accordance with an embodiment of the present invention.
Figure 10:
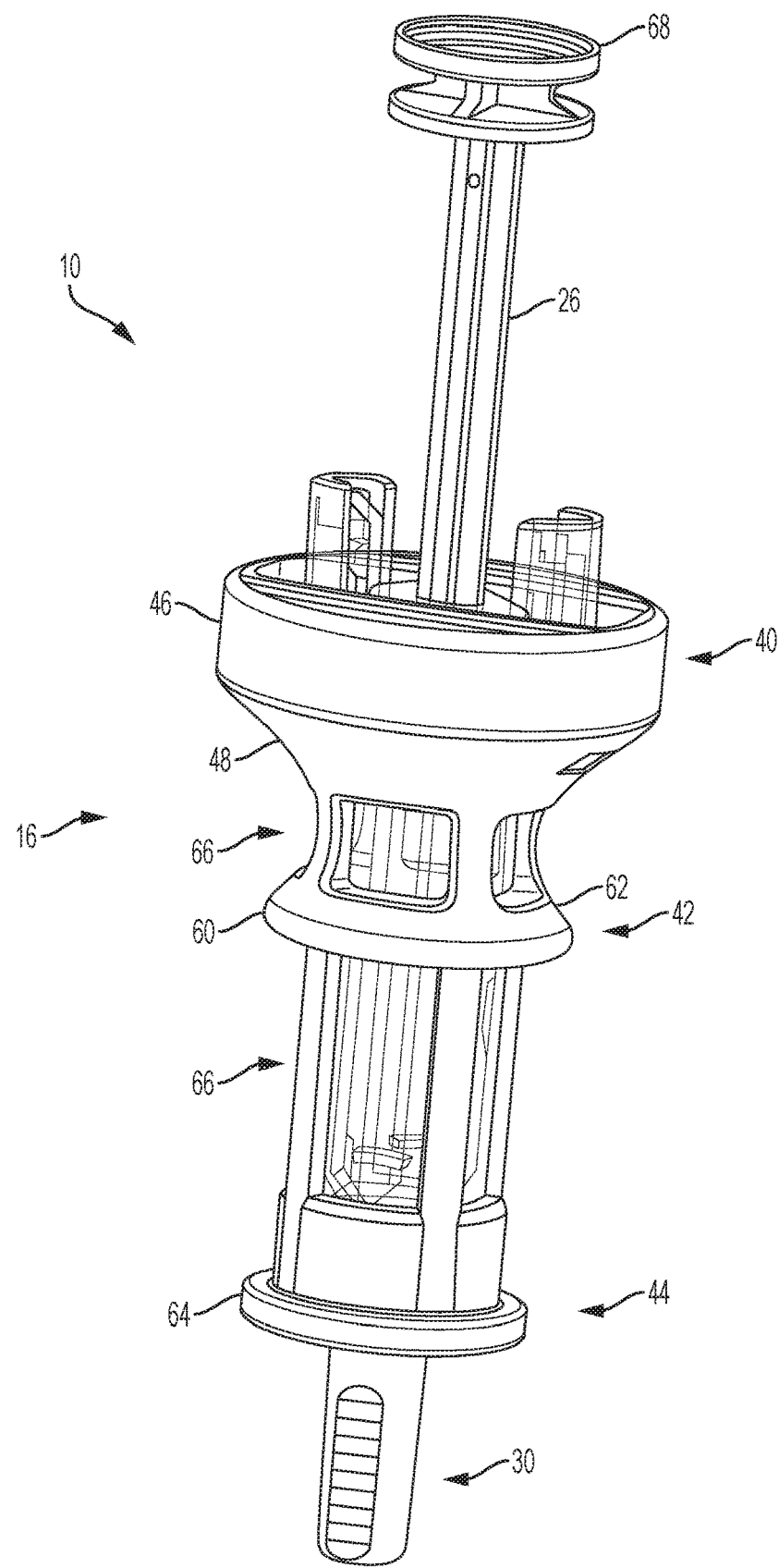
FIG. 10 is a perspective view of a medical injector with a cap in accordance with an embodiment of the present invention.
Figure 11:
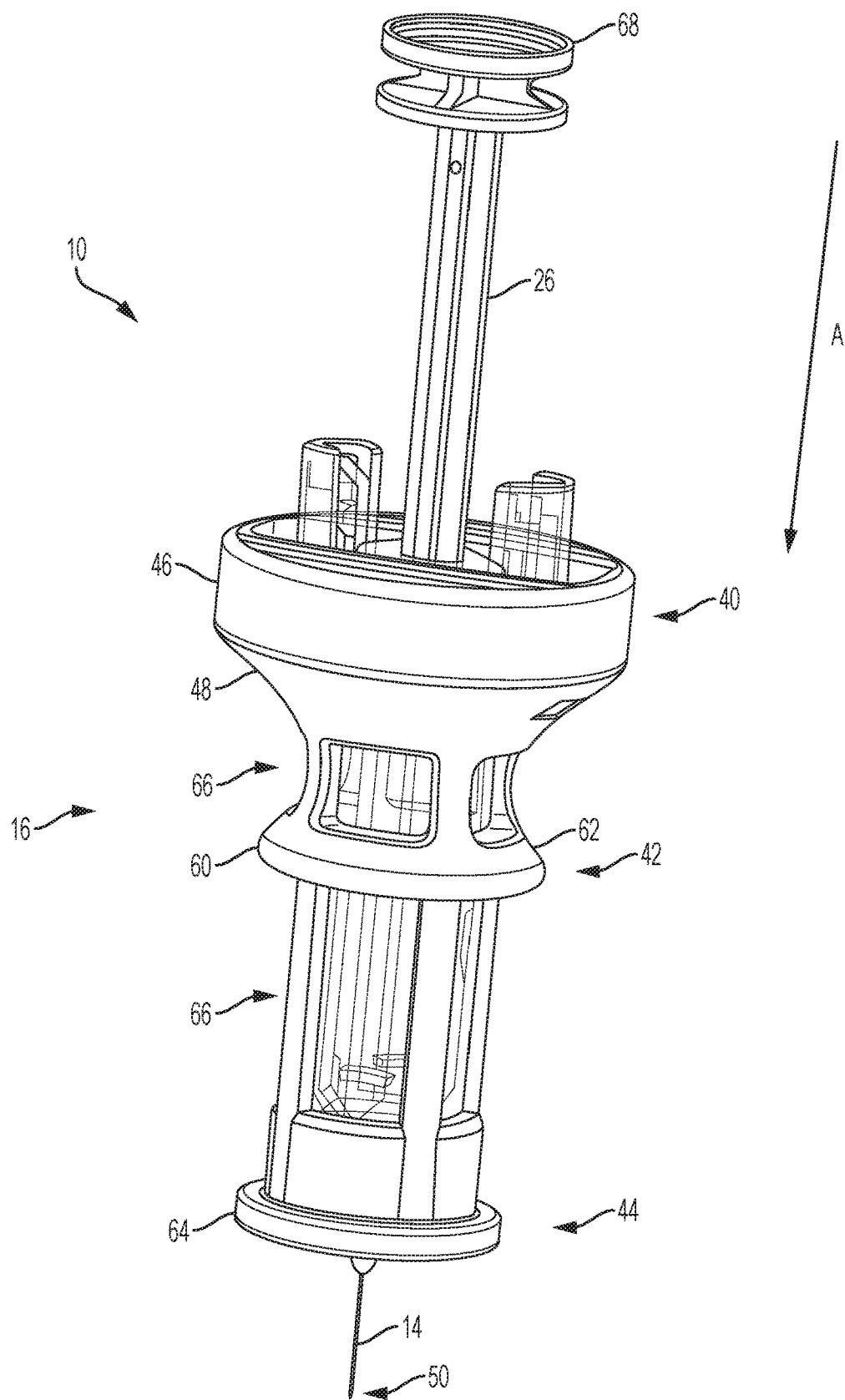
FIG. 11 is a perspective view of a medical injector in accordance with an embodiment of the present invention.
Figure 12:
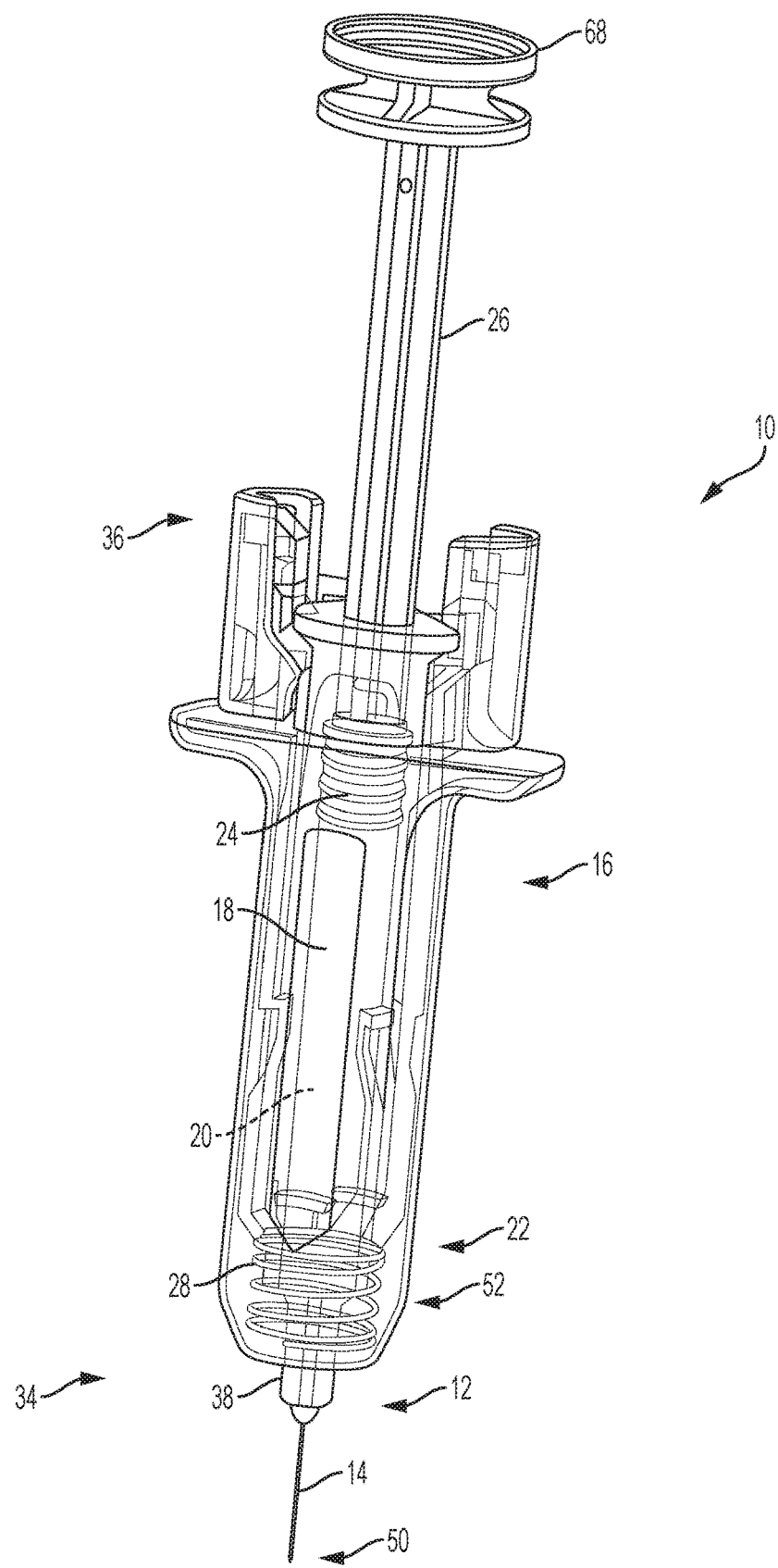
FIG. 12 is a cross-sectional view of a medical injector in accordance with an embodiment of the present invention.

FIGS. 1-12 illustrate an exemplary embodiment of the present disclosure. Referring to FIGS. 1-9, a cap remover or a second cap 32 of the present disclosure is illustrated. Referring to FIGS. 9-12, in one embodiment, a medical injector 10 of the present disclosure includes a first cap 30 and a second cap or cap remover 32. The first cap 30 may be formed of a plastic and/or rubber guard material. Referring to FIGS. 10-11, the first cap 30 shields and covers a distal end 50 of a needle 14. Referring to FIG. 9, the second cap or cap remover 32 shields and covers the distal end 50 of the needle 14 and the first cap 30. In one embodiment, the second cap 32 may be formed from a harder material than the first cap 30 such that the second cap 32 provides a protective covering for the first cap 30 when the second cap 32 shields the first cap 30. In another embodiment, the second cap 32 may be the only cap that shields and covers the distal end 50 of the needle 14.

In one embodiment, with the first cap 30 covering the distal end 50 of the needle 14 and with the second cap 32 covering the distal end 50 of the needle 14 and the first cap 30, the second cap 32 is engaged with the first cap 30 via a friction fit such that removal of the second cap 32 simultaneously removes the first cap 30 from the distal end 50 of the needle 14.

Referring to FIGS. 9-12, a medical injector 10 includes a needle assembly 12 having a needle 14, an injector housing 16, a barrel 18 having a reservoir 20 for medicament sealed by a septum 22, a stopper 24, a plunger rod 26 having a flange 68, a spring 28, a first cap 30, and a second cap or a cap remover 32.

The medical injector 10 includes a distal end 34 and a proximal end 36. The reservoir 20 of the barrel 18 is encased within the injector housing 16. In one embodiment, the reservoir 20 may be defined by the injector housing 16. In another embodiment, the reservoir 20 may be defined by a separate component contained within the injector housing 16, e.g., a cartridge or barrel. The needle assembly 12 includes a needle 14 and a hub 38. The needle 14 includes a distal end 50, formed for insertion into a patient, and a proximal end 52.

The medical injector 10 of the present disclosure may be of various forms, including being a syringe, self-injector, auto-injector, or pen injector. In one embodiment, the medical injector 10 is well-suited for administering at least one fixed dose. In another embodiment, the medical injector 10 is well-suited for administering a series of fixed doses. The medical injector 10 may be configured in any way known to be compatible with the plunger rod 26. The medical injector 10 may include a reservoir 20 for accommodating an injectable medicament, which may be a drug cartridge or formed directly in the medical injector 10. The reservoir 20 may have one or more stoppers 24 associated therewith.

Referring to FIGS. 9-11, the injector housing 16 of the medical injector 10 includes an upper guard 40, a lower guard 42, and a base 44. The upper guard 40 includes a first flange 46 and a first tapered wall 48. In one embodiment, the upper guard 40 provides a gripping component that includes surfaces for accommodating a user's fingers, such as finger grip indentations or similar structure. For example, the upper guard 40 provides ergonomically shaped surfaces that substantially conform to a user's fingertips to aid the user in manipulating the medical injector 10 and using the medical injector 10 in a medical procedure, and may provide multiple finger grip positions for the user. The upper guard 40 allows a user to handle and/or grip the medical injector 10 in a variety of different ways.

The lower guard 42 includes a second flange 60 and a second tapered wall 62. The lower guard 42 provides a second gripping component that includes surfaces for accommodating a user's fingers, such as finger grip indentations or similar structure. In one embodiment, the lower guard 42 provides a user with vertical stability in hand, precisely during needle insertion with the medical injector 10.

The upper guard 40 and the lower guard 42 together provide a gripping component that includes surfaces for accommodating a user's fingers to aid the user in manipulating the medical injector 10 and using the medical injector 10 in a medical procedure.

The base 44 includes a flange 64 that contacts the skin of a user during use of the medical injector 10. The base 44 provides a stability component that stabilizes the medical injector 10 on a user's skin during use of the medical injector 10. In one embodiment, the base 44 also hides the spring 28.

Referring to FIG. 9-11, the injector housing 16, the upper guard 40, the lower guard 42, and the base 44 are configured to provide viewing windows 66. The viewing windows 66 allow a user to see the barrel 18 that includes the medicament.

Referring to FIG. 10, a first cap 30 shields and covers the distal end 50 of the needle 14. Referring to FIG. 9, the second cap or cap remover 32 shields and covers the distal end 50 of the needle 14 and the first cap 30. In one embodiment, the second cap 32 may be the only cap that shields and covers the distal end 50 of the needle 14.

Referring to FIGS. 1-9, the second cap or cap remover 32 includes a body 100 having a distal end 101, a proximal end 102, a cylindrical portion 104 adjacent the proximal end 102, and a hemispherical portion 106 adjacent the distal end 101.

The hemispherical portion 106 includes an outer wall 110, an inner wall 112, a distal flange 114, a first cavity 116, and a distal wall 118.

The outer wall 110 of the hemispherical portion 106 provides a gripping component that includes surfaces for accommodating a user's fingers, such as finger grip indentations or similar structure. For example, the outer wall 110 of the hemispherical portion 106 provides ergonomically shaped surfaces that substantially conform to a user's fingertips to aid the user in handling and grasping the second cap 32.

In one embodiment, the outer wall 110 of the hemispherical portion 106 includes finger grip indentations 120 for providing a gripping component for accommodating a user's fingers. The finger grip indentations 120 improve the grip between the second cap 32 and the user's fingertips. In one embodiment, the finger grip indentations 120 are formed as a plurality of ribs 122 and troughs 124 extending along the periphery of the outer wall 110 of the hemispherical portion 106. In one embodiment, the finger grip indentations 120 are formed as a plurality of alternating ribs 122 and troughs 124 extending circumferentially about the periphery of the outer wall 110 of the hemispherical portion 106. The hemispherical portion 106 may terminate at a distal flange 119 having a substantially flat distal distally directed surface.

In one embodiment, the alternating ribs 122 and troughs 124 are integrally formed with the second cap 32 and provide a visual and tactile cue to the user to instruct the user where to place his or her fingertips.

In one embodiment, the shape of the second cap 32 is designed to help disabled people more easily and more conveniently handle the second cap 32 and/or the medical injector 10.

Figure 2:
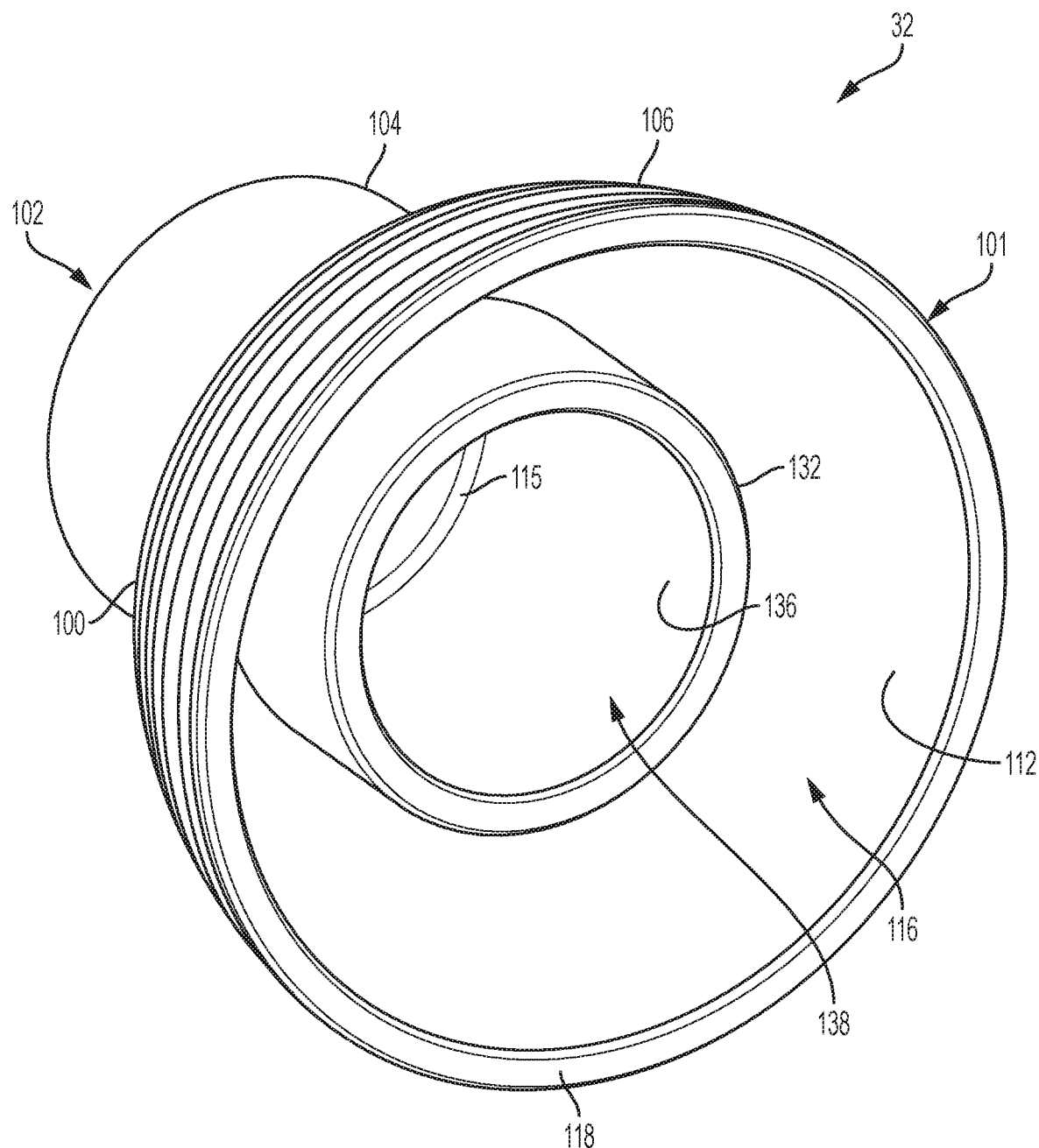
FIG. 2 is a perspective view of a cap remover in accordance with an embodiment of the present invention.

The cylindrical portion 104 includes an outer cylindrical portion 130, an inner cylindrical portion 132, an outer wall 134, and inner wall 136, defining a second cavity 138. The cylindrical portion 104 provides a secure attachment of the second cap 32 to the distal end 34 of the medical injector 10 as shown in FIG. 9. Referring to FIG. 1, the outer cylindrical portion 130 defines a passageway in communication with an opening in the hemispherical portion 106 and extends proximally from an exterior surface of the hemispherical portion 106. Referring to FIG. 2, the inner cylindrical portion 132 defines a passageway in communication with the opening in the hemispherical portion 106 and extends into the cavity 116 defined by the hemispherical portion 106. In one embodiment, the outer cylindrical portion 130 may include a metallic ring integrated therewith.

Referring to FIG. 2, the inner wall 136 of the cylindrical portion 104 defines a second cavity 138 in the proximal end 102 of the cylindrical portion 104. Referring to FIG. 2, the outer wall 134 of the inner cylindrical portion 132 and the inner wall 112 of the hemispherical portion 106 define the first cavity 116 therebetween.

The second cavity 138 is sized and shaped to receive at least a portion of the first cap 30 therein. A protrusion 115 may extend inwardly from the interior wall 136 toward a longitudinal axis of the body 100. In one embodiment, the protrusion 115 is an annular ring. In another embodiment, a plurality of circumferentially spaced protrusions 115 extend inwardly from the interior wall 136 toward a longitudinal axis of the body 100. The protrusion 115 may include a tapered proximal surface 140 angled from the interior wall 136 inwardly toward the longitudinal axis of the body 100 and downwardly toward the distal end 101 of the body 100 for aiding the second cap 32 in sliding over the first cap 30.

With the first cap 30 covering the distal end 50 of the needle 14 and with the second cap 32 covering the distal end 50 of the needle 14 and the first cap 30, the second cap 32 is engaged with the first cap 30 such that removal of the second cap 32 simultaneously removes the first cap 30 from the distal end 50 of the needle 14. In one embodiment, the second cap or the cap remover 32 is removed from the medical injector 10 by applying a distally directed force F to the second cap or cap remover 32, as shown in FIG. 9.

In one embodiment, the hemispherical portion 106 of the second cap 32 provides the above-described gripping component. In one embodiment, the hemispherical portion 106 of the second cap 32 provides ergonomically shaped surfaces that improve the grip between the second cap 32 and the user's fingertips to aid the user in removing the second cap 32 from the distal end 50 of the needle 14 and/or to aid the user in simultaneously removing the second cap 32 and the first cap 30 from the distal end 50 of the needle 14.

In one embodiment, the second cap 32 allows a user to handle the second cap 32 without finger flexion. In one embodiment, the hemispherical portion 106 of the second cap 32 provides a gripping component that allows a user to better handle the second cap 32 and/or the medical injector 10.

When it is desired to use the medical injector 10 of the present disclosure, the second cap 32 is used to easily remove the second cap 32 and the first cap 30 from the distal end 50 of the needle 14 simultaneously. Referring to FIG. 11, with the caps 30, 32 removed, the distal end 50 of the needle 14 is exposed and ready to be positioned adjacent a desired portion of the skin of a user. In one embodiment, the second cap 32 may be the only cap that shields and covers the distal end 50 of the needle 14.

When it is desired to expel or deliver the medication contained within the barrel 18 of the medical injector 10, and with the medical injector 10 properly used to contact and pierce the skin of a user, the flange 68 of the plunger rod 26 and a portion of the injector housing 16 can be grasped, e.g., with the user's thumb on the flange 68 of the plunger rod 26 and with the user's fingers extending around the first flange 46 of the upper guard 40 of injector housing 16. In this manner, the medical injector 10 can be grasped by a user in a well-known and well-recognized manner similar to the operation of a conventional hypodermic syringe. Next, the user effects a squeezing movement between the thumb on the flange 68 of the plunger rod 26 and four fingers grasping the first flange 46 of the upper guard 40, thereby causing the plunger rod 26 to move in a direction generally along arrow A (FIG. 11).

Movement of the plunger rod 26 in the direction generally along arrow A actuates movement of the stopper 24 in the direction generally along arrow A toward the distal end 34 of the medical injector 10. In this manner, movement of the stopper 24 in the direction generally along arrow A forces the medicament fluid contained within the reservoir 20 of the barrel 18 to be forced out the distal end 50 of the needle 14 and into the user and/or patient.

After injection of the medicament fluid, the needle 14 can be removed from the skin of the patient. In one embodiment, the medical injector 10 may include an automatic retraction mechanism for moving the needle 14 into the injector housing 16 for safe shielding of the needle 14 after use. In one embodiment, the spring 28 may be used as part of the automatic retraction mechanism.

All of the components of the medical injector 10 may be constructed of any known material, and are desirably constructed of medical-grade polymers.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A cap remover for removing a cap from a needle of a medical injector, the cap remover comprising:
   a cap remover body having a proximal end and a distal end, the cap remover body comprising:
   a hemispherical member having an interior surface defining a cavity within the distal end of the cap remover body and an exterior surface including a gripping component; and
   a cylindrical member extending into the cavity of the hemispherical member and defining a passageway in communication with an opening in the hemispherical member,
   wherein with the cap received within the cylindrical member, the cylindrical member is configured to engage the cap such that removal of the cap remover from the medical injector simultaneously removes the cap from the needle of the medical injector to prepare the medical injector for use.

2. The cap remover of claim 1, further comprising a protrusion extending inwardly from an interior wall of the cylindrical member.

3. The cap remover of claim 2, wherein the protrusion is adapted to frictionally engage the cap.

4. The cap remover of claim 3, wherein with the protrusion of the cap remover body engaged with the cap, the cap remover body is configured to disengage the cap from the medical injector upon application of a distally directed force to the cap remover body.

5. The cap remover of claim 3, wherein the protrusion includes a tapered proximal surface angled inwardly towards a longitudinal axis of the cap remover body.

6. The cap remover of claim 2, wherein the protrusion comprises an annular ring.

7. The cap remover of claim 1, wherein the gripping component comprises a plurality of ribs and a plurality of troughs alternating from a proximal end of the hemispherical member to a distal end of the hemispherical member.

8. The cap remover of claim 1, wherein the hemispherical member further comprises a flange having a substantially flat distally directed surface.

9. The cap remover of claim 1, wherein the hemispherical member has a first diameter and a second diameter located distally of the first diameter, the second diameter being larger than the first diameter.

10. The cap remover of claim 1, wherein the gripping component is configured for accommodating at least a portion of a user's fingers to aid in handling the cap remover.

11. The cap remover of claim 1, wherein the cap remover comprises a second material and the cap of the medical injector comprises a first material, wherein the first material is different than the second material.

12. The cap remover of claim 11, wherein the second material is harder than the first material.

13. The cap remover of claim 1, wherein the gripping component comprises at least one rib and at least one trough integrally formed with the hemispherical member.

14. The cap remover of claim 1, wherein the hemispherical member is adjacent to the distal end of the cap remover body.

15. The cap remover of claim 1, further comprising a second cylindrical member defining a passageway in communication with the opening and extending from the exterior surface of the hemispherical member.

\* \* \* \* \*